(12) United States Patent
Barnell

(10) Patent No.: US 11,617,630 B2
(45) Date of Patent: Apr. 4, 2023

(54) MEDICAL DEVICE PACKAGING SYSTEMS AND METHODS

(71) Applicant: Medtronic Vascular, Inc., Santa Rosa, CA (US)

(72) Inventor: Jeffrey Barnell, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 519 days.

(21) Appl. No.: 16/787,783

(22) Filed: Feb. 11, 2020

(65) Prior Publication Data

US 2020/0275987 A1 Sep. 3, 2020

Related U.S. Application Data

(60) Provisional application No. 62/812,604, filed on Mar. 1, 2019.

(51) Int. Cl.
*B65D 75/28* (2006.01)
*A61B 50/33* (2016.01)
*A61B 50/30* (2016.01)
*A61B 50/00* (2016.01)

(52) U.S. Cl.
CPC .......... *A61B 50/33* (2016.02); *A61B 50/3001* (2016.02); *A61B 2050/002* (2016.02); *A61B 2050/0065* (2016.02); *A61B 2050/314* (2016.02)

(58) Field of Classification Search
CPC ...... A61B 2050/0065; A61B 2050/314; A61B 2050/318; A61B 2050/002; A61B 2017/00362; A61B 50/3001; A61B 50/33
USPC ................................ 206/438, 484, 570, 363
See application file for complete search history.

(56) References Cited

U.S. PATENT DOCUMENTS

| | | | | |
|---|---|---|---|---|
| 6,010,462 A | * | 1/2000 | Stoermer, III | ....... B65D 77/245 600/572 |
| 2014/0131369 A1 | * | 5/2014 | Scovell | .................. B65D 77/02 53/473 |
| 2019/0060050 A1 | | 2/2019 | Barnell | |

* cited by examiner

*Primary Examiner* — King M Chu
(74) *Attorney, Agent, or Firm* — Brooks Kushman P.C.

(57) ABSTRACT

A method includes hermetically sealing a medical device within a pouch, the pouch including peeling panels that are free from one another. The pouch is placed within a tray and the peeling panels are attached to unloading handles of the tray. The unloading handles are releasably coupled together. The method further includes simultaneously separating the unloading handles and the peeling panels to open the pouch and expose the medical device for removal thereof.

15 Claims, 9 Drawing Sheets

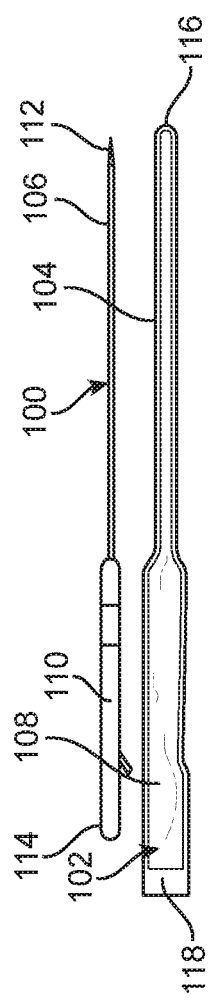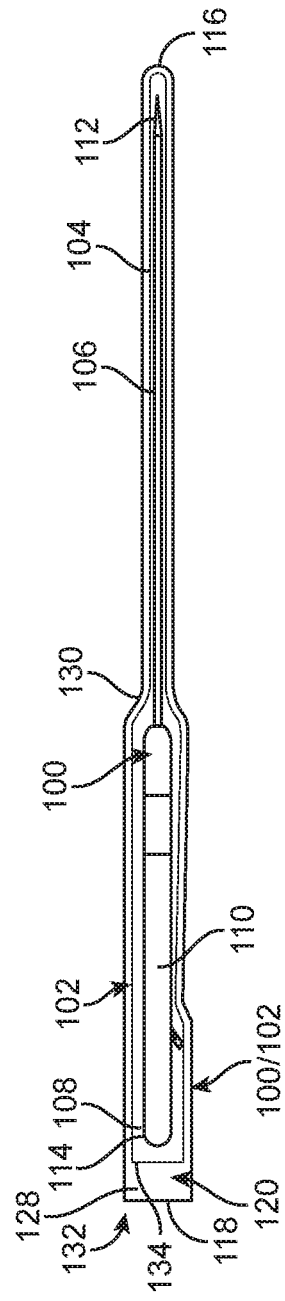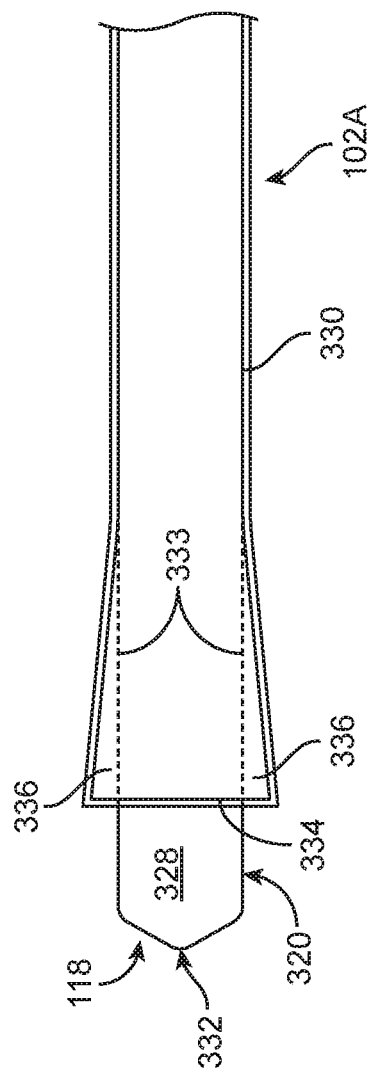

MEDICAL DEVICE PACKAGING SYSTEMS AND METHODS

CROSS-REFERENCE TO RELATED APPLICATIONS

This application claims the benefit of U.S. Provisional Application No. 62/812,604 filed on Mar. 1, 2019, entitled "MEDICAL DEVICE PACKAGING SYSTEMS AND METHODS" of Jeffrey Barnell et al., which is incorporated herein by reference in its entirety.

FIELD

The present technology is generally related to medical device packaging systems and methods.

BACKGROUND

Sealed pouches are used by medical device manufacturers to create a sterile barrier around the terminally sterilized device. The typical pouch generally includes two rectangular sheets of extruded multilayer film and/or Tyvek heat sealed at the linear edge of the film on three sides, leaving one side open for the insertion of the device. After the product is inserted, the remaining side is hermetically sealed. Once sterilized, the rectangular pouch serves as the sole component keeping the product sterile prior to use.

Although flat rectangular pouches accommodate products that are essentially 2-dimensional, such as a coronary stent, they are not optimally spatialized for products with substantial 3-dimensional volume, such as an aortic stent graft or transcatheter heart valve delivery system. In the conventional design, the rectangular pouch must not only be sized to the largest cross section of the device, it must also be significantly longer than the device to accommodate performing the final seal. The pouched device is then placed in a carton for shipping. If the carton was sized to the outer dimension of the pouch, not only would the carton be excessive large, wasteful and expensive, the device would be subjected to damaging movements during distribution. In practice the carton is sized smaller than the pouch. The excess pouch material that does not lay flat in the carton results in folds or pleats as the sealed rectangular pouch is placed in a box. The folds create stress risers in the film that, when subjected to vibration and impacts during shipment, increase the potential for fatigue, stress cracking, delamination, and pin holes in the sterile barrier film. The actual barrier layer in the pouch may be very thin, such as only 0.001" thick. The presence of folds may be a predominant cause of sterile barrier failure during validation testing.

Impacts and vibration during shipping/distribution can cause the conventional shelf carton, pouch(es), internal tray, and device to move relative to each other. The opposing movements and energy differentials can cause the pouch to abrade or puncture resulting in a sterile barrier breach. The situation is more acute for long delivery systems, devices with significant thicknesses relative to its foot print, or any medical device, where its weight, center of gravity, and dimensions accentuate the forces and movement.

In these terminally sterilized medical device applications, thermoformed trays are typically used to hold the device within a single or double sterile barrier pouch(es). The pouch solely establishes the sterile barrier, while in this arrangement is also the most susceptible to damage.

SUMMARY

The techniques of this disclosure generally relate to a packaging system having a tray. The tray includes a rigid distal portion, opposed unloading handles, and a flex feature allowing the unloading handles to move relative to the rigid distal portion.

In one aspect, the present disclosure provides a packaging system including a profiled pouch for a medical device. The profiled pouch includes two shaped sheets sealed on three sides by a linear seal. The linear seal leaves a pouch opening open for insertion of the medical device. A profile of the profiled pouch matches a profile of the medical device.

In another aspect, the present disclosure provides a method including hermetically sealing a medical device within a pouch, the pouch including peeling panels that are free from one another. The pouch is placed within a tray and the peeling panels are attached to unloading handles of the tray. The unloading handles are releasably coupled together. The method further includes simultaneously separating the unloading handles and the peeling panels attached thereto to open the pouch and expose the medical device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 1 is a top view of a medical device and a profiled pouch in accordance with one embodiment.

FIG. 2 is a top view of the medical device in the profiled pouch of FIG. 1 in accordance with one embodiment.

FIG. 3 is a top view of a profiled pouch having a flared peeling portion in accordance with another embodiment.

DETAILED DESCRIPTION

Figure 4:
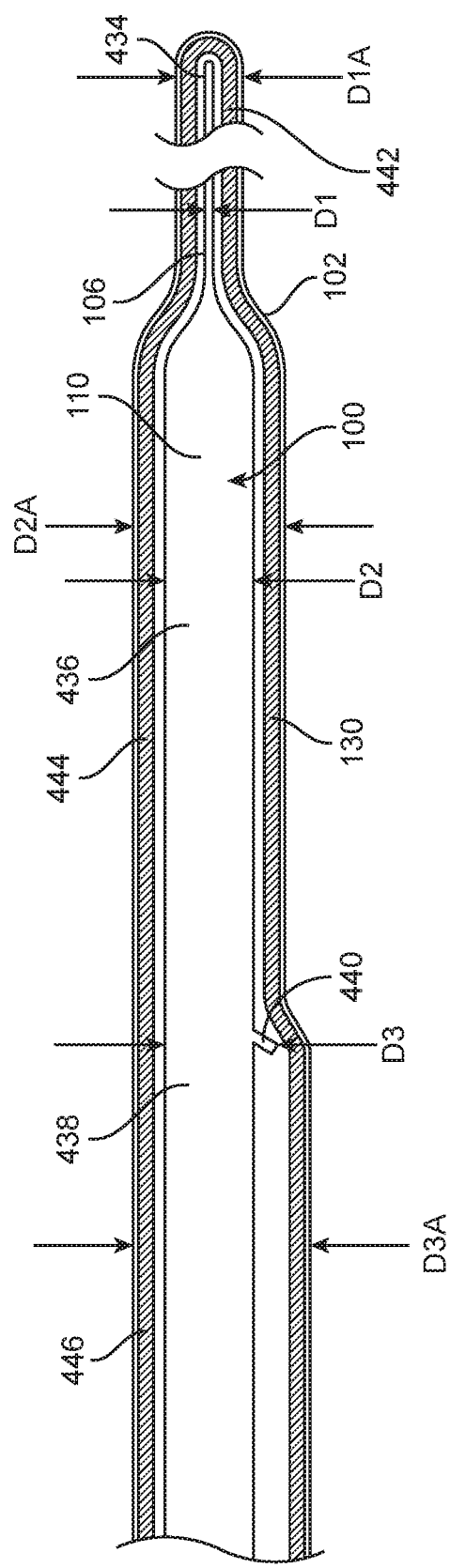
FIG. 4 is a schematic of the profiled pouch of FIGS. 1 and 2 in accordance with an embodiment.

Multiple packaging systems and methods are disclosed. One of ordinary skill in the art will understand that the systems and methods may be utilized alone or in combination with each other. The packaging systems are described in the context of medical devices; however, they are suitable for any type of device. In addition, any specific medical device that is mentioned is merely an example, and is not intended to be limiting.

Profiled Pouch

The disclosed profiled pouch, which may be referred to as the Profiled Sterile Barrier Pouch (PSBP), may minimize stress risers by adjusting the placement of the edge seals along the length of the pouch. The interior pouch dimensions may be made to correspond to the cross section of the device. In practice, the seals may roughly follow the profile for the device, however, this is not required. Seal placement may consider asymmetric device features, transitions between cross sections, sharp features protruding from the device such as liquid or gas hose connections and loading/unloading paths. In one embodiment, the PSBP may be asymmetric to account for the asymmetric device features. The PSBP may have a shape that corresponds to the profile of the device (e.g., traces/follows an outer profile of the device).

FIG. 1 is a top view of a medical device 100, e.g., a branch device, and a profiled pouch 102 in accordance with one embodiment. FIG. 2 is a top view of medical device 100 in profiled pouch 102 of FIG. 1 in accordance with one embodiment.

Profiled pouch 102 is an example of a PSBP that may be used for device 100. Profiled pouch 102 is sometimes referred to as PSBP 102. As shown, profiled pouch 102 is shaped such that the pouch profile corresponds to the profile of device 100. As shown, there is less material used in profiled pouch 102 as compared to a conventional rectangular pouch.

With reference to FIG. 2, an example of profiled pouch 102 with device 100 inside is shown. Compared to the conventional rectangular pouch, there is very little folding of the material in profiled pouch 102, which reduces stress risers. Profiled pouch 102 substantially matches the shape of device 100, including a narrow-elongated portion 104 that contains a sheath 106 of delivery device 100 (right side) and a wider portion 108 that contains a handle 110 of device 100 (left side).

As used herein, a distal end 112 of device 100 is identified as the end that is farthest from the operator (handle 110) while a proximal end 114 of device 100 is the end nearest the operator (handle 110). Similarly, a distal end 116 of a profiled pouch such as profiled pouch 102 is identified to the end that is farthest from handle 110 and adjacent distal end 112 of device 100 while a proximal end 118 of a profiled pouch such as profiled pouch 102 is the end nearest handle 110 and adjacent proximal end 114 of device 100. Further, a distal end of a tray and system such as the tray and system discussed below is identified to the end that is farthest from handle 110 and adjacent distal end 112 of device 100 while a proximal end of the tray and system is the end nearest handle 110 and adjacent proximal end 114 of device 100.

Profiled pouch 102 includes a peeling portion 120 including peeling panels 128 used to peel open profiled pouch 102. Suitable, profiled pouch 102 includes two shaped sheets of extruded multilayer film and/or Tyvek heat sealed at the linear edge on three sides, as indicated by a linear seal 130. Linear seal 130 leaves a pouch opening 132 open for the insertion of device 100. After device 100 is inserted, the remaining side (pouch opening 132) is hermetically heat sealed by an opening seal 134.

As illustrated, peeling panels 128 of peeling portion 120 extend proximally from opening seal 134. Peeling panels 128 are free from one another, i.e., are not bound together except at opening seal 134. Accordingly, the user, e.g., circulating nurse, can easily grasp peeling panels 128 and pull peeling panels 128 apart. This peels opening seal 134 apart opening pouch opening 132 for removal of device 100.

FIG. 3 is a top view of a profiled pouch 102A having a flared peeling portion 320 in accordance with another embodiment. Profiled pouch 102A of FIG. 3 is similar to profiled pouch 102 of FIGS. 1 and 2 and only the significant differences are discussed below.

With reference to FIG. 3, in addition to the applications previously stated, for some therapies, it may be desirable to increase a pouch opening 332 to assist in the removal of the device 100 during aseptic transfer. Profiled pouch 102A can accommodate this requirement by allowing the designer to widen the faces near proximal end 118 of profiled pouch 102A where pouch opening 332 is. Accordingly, proximal end 118 of profiled pouch 102A may have flared peeling portion 320, an example of which is shown in FIG. 3.

The imaginary lines 333 represent extensions of the non-flared portion of profiled pouch 102A, such that wide mouth portions 336 above and below the lines 333 are the widened or flared portions that provide extra room for grasping and removal of device 100. The region where flared peeling portion 320 ends and meets the narrower portion on the left side may be referred to as the peel zone.

Flared peeling portion 320 includes wide mouth portions 336 and peeling panels 328 used to peel open profiled pouch 102A. Suitable, profiled pouch 102A includes two shaped sheets of extruded multilayer film and/or Tyvek heat sealed at the linear edge on three sides, as indicated by a linear seal 330. Linear seal 330 leaves pouch opening 332 open for the insertion of device 100. After device 100 is inserted, the remaining side (pouch opening 332) is hermetically heat sealed by an opening seal 334.

As illustrated, peeling panels 328 of flared peeling portion 320 extend proximally from opening seal 334. Peeling panels 328 are free from one another, i.e., are not bound together except at opening seal 334. Accordingly, the user, e.g., the circulating nurse, can easily grasp peeling panels 328 and pull peeling panels 328 apart. This peels opening seal 334 apart opening pouch opening 322 for removal of device 100.

Figure 5:
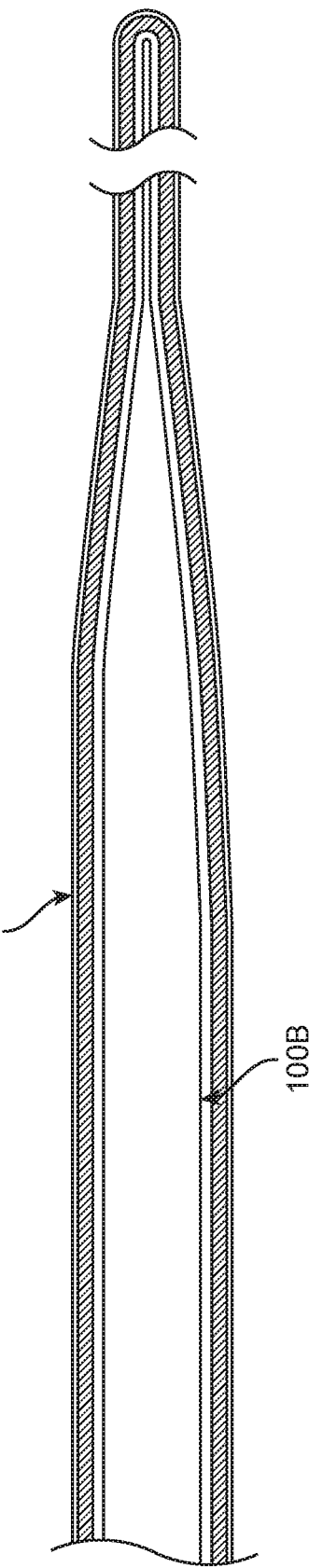
FIG. 5 is another schematic of a profiled pouch in accordance with another embodiment.

FIG. 4 is a schematic of profiled pouch 102 of FIGS. 1 and 2 in accordance with an embodiment. FIG. 5 is another schematic of a profiled pouch 102B in accordance with another embodiment.

With reference to FIGS. 4 and 5, example top views of different pouch profiles are shown. These pouch profiles are only examples, however, and the profile may change based on the device being held by the pouch.

Paying particular attention to FIG. 4, device 100 has a first profile 434 corresponding to sheath 106 having a first dimension D1. Device 100 has a second profile 436 corresponding to handle 110 having a second dimension D2. Device 100 has a third profile 438 corresponding to a port 440, e.g., a flush port, having a third dimensions D3. Dimensions D1, D2, D3 are measured in a direction perpendicular to a length of device 100.

In accordance with this embodiment, dimension D1 is less than dimension D2, and dimension D2 is less than dimension D3. In other words, device 100 has the smallest dimension D1 at distal end 112 and has the greatest dimension D3 at port 440. This is sometimes referred to as the profile of device 100. Although a particular profile is set forth, device 100 can have other profiles depending upon the application.

Profiled pouch 102 has a profile that matches the profile of device 100. Specifically, profiled pouch 102 has a distal portion 442 surrounding sheath 106 that has a dimension D1A slightly larger than dimension D1 of device 100. Profiled pouch 102 has a middle portion 444 surrounding handle 110 that has a dimension D2A slightly larger than D2 of device 100. Finally, profiled pouch 102 has a proximal portion 446 surrounding handle 110 including port 440 that has a dimension D3A slightly larger than dimension D3 of device 100. As used herein, slightly larger means having a dimension that is close to but slightly greater than the dimension of device 100 such that device 100 fits snuggly within pouch 102 but still has some space to allow device 100 to be removed from pouch 102.

To allow device 100 to be readily removed from profiled pouch 102, profiled pouch 102 is not reduced from any particular dimension proximally. For example, once profile pouch 102 increases from dimension D2 to dimension D3, profiled pouch 102 has at least dimension D3 to proximal end 118. If the dimension was reduced, a waist would be created preventing device 100 from being easily removed. To illustrate, if profiled pouch 102 had a dimension less than dimension D3 of port 440 between port 440 and proximal end 118 of profiled pouch 102, port 440 would not be able to pass through the constriction (waist) without tearing profiled pouch 102.

Although particular profiles are illustrated for device 100 and profiled pouch 102, in another embodiment, device 100 and/or profiled pouch 102 has other shapes. For example, some devices benefit from a pouch having a shape that does not mirror the profile of the device directly but removes folds in the pouch. In one specific embodiment, the pouch is hour-glass shaped.

FIG. 5 illustrates profiled pouch 102B having a slightly different profile than profiled pouch 102 of FIG. 4. For example, profiled pouch 102B goes from a first dimension to a larger second dimension matching the profile of a device 100B that goes from a first dimension to a larger second dimension.

The profiled pouch in accordance with an embodiment, which may be an asymmetric pouch, may utilize existing manufacturing processes to create a profiled pouch that improves the volumetric compatibility between the device and the profiled pouch. The material that would have previously concentrated stress at the folds is marginalized. The design reduces the carton size and material usage, thereby potentially lowering manufacturing and distribution costs. The profiled pouch in combination with the Exo Tray concept, designed in more detail below, may further improve sterile barrier robustness and cost.

The profiled pouch utilizes a design approach that minimizes the occurrence of stress risers. A reduction in stress risers has been proven to increase the robustness of the sterile barrier. Techniques have been developed to optimize the path of the edge seals for a specific device shape. Material control welds may be used to further define how the pouch material lays in the carton. Independent of the sterile barrier seal, profiles and welds can be placed on the pouch that maintains it in a suitable placement within the tray.

In applications where the tray and device are placed inside the profiled pouch, the design can eliminate excess material and improve the robustness of the sterile barrier. The design must then consider the tray characteristics in addition to the device. Elements that control movement within the carton or movement of the tray within the profiled pouch are possible.

When used in conjunction with the Exo Tray Packaging System (described below), the profiled pouch may reduce the likelihood of device contamination, while also speeding up the aseptic transfer process. The peel end of the pouch may be fixed to the Exo Tray handles to enable better control of the device, while completing the process of opening the pouch and presenting the device into the sterile field in one continuous motion. The profiled pouch is a general-purpose solution to improve the spatial compatibility between 2-D web pouches and 3-D devices. The approach leverages existing commercial pouch manufacturing techniques, thereby eliminating process development and vendor investment.

The profiled pouch may be less expensive than the equivalent rectangular pouch. The cost of the carton and distribution may also be less due to the reduced size and weight. The profiled pouch may be cost-effective for low volume indications and may provide a superior option to traditional flat pouches and at a lower unit cost.

Exo Tray Packaging System

Figure 6:
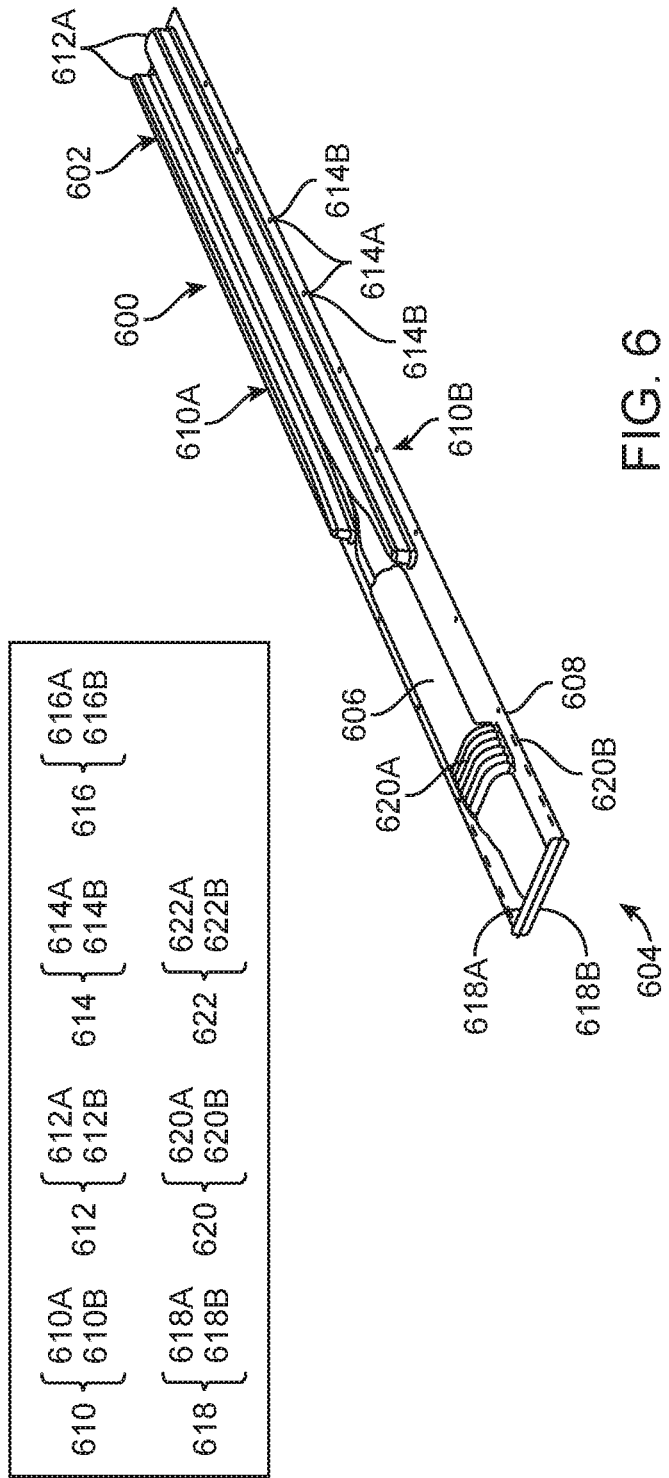
FIG. 6 is a perspective view of an exo tray packaging system including a tray for containing a medical device and a profiled pouch in accordance with an embodiment.
Figure 7:
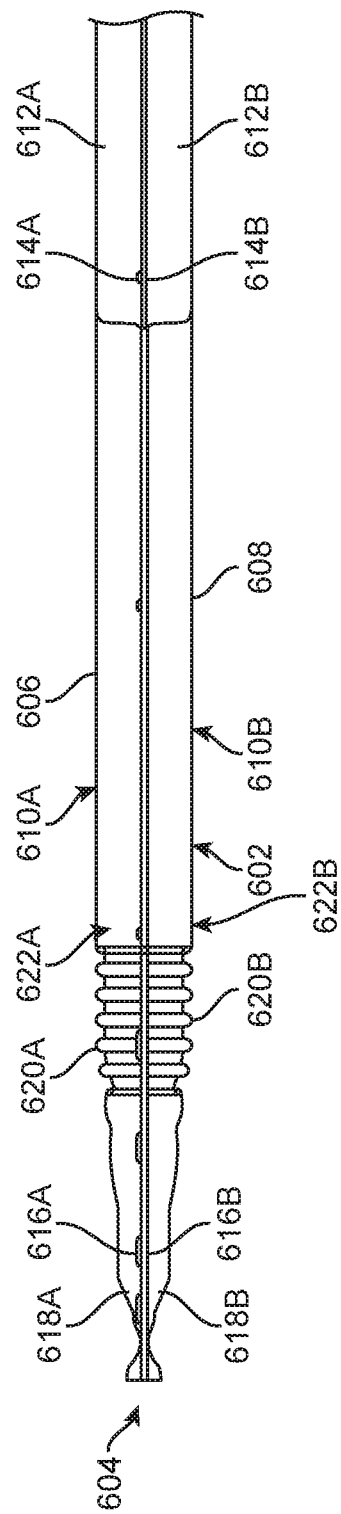
FIG. 7 is a side view of the tray of FIG. 6 in accordance with an embodiment.
Figure 8:
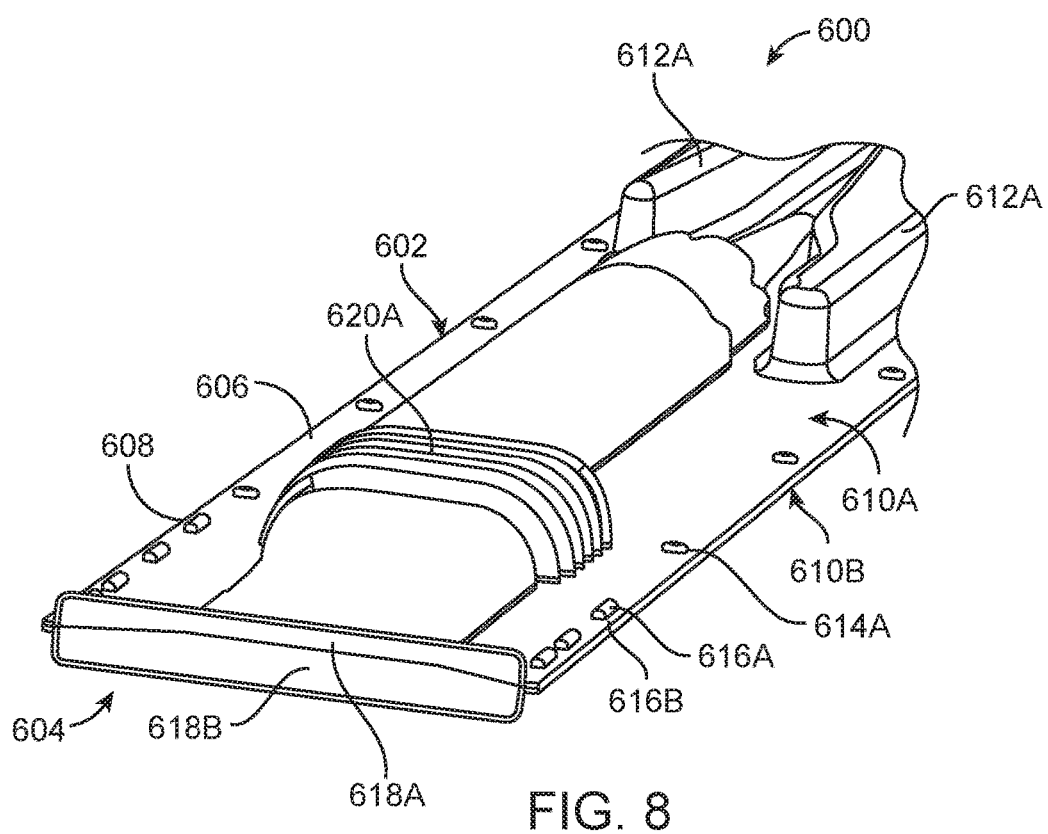
FIG. 8 is an enlarged perspective view of a proximal end of the tray of FIGS. 6 and 7 in accordance with an embodiment.

FIG. 6 is a perspective view of an exo tray packaging system 600 including a tray 602 for containing a medical device and profiled pouch, such as device 100 and profiled pouch 102 of FIG. 2, in accordance with an embodiment. FIG. 7 is a side view of tray 602 of FIG. 6 in accordance with an embodiment. FIG. 8 is an enlarged perspective view of a proximal end 604 of tray 602 of FIGS. 6 and 7 in accordance with an embodiment.

With reference to FIGS. 2, 6-8, in this system 600, a medical device such a device 100 is first placed and sealed within a pouch such as profiled pouch 102 and then the device and profiled pouch are placed inside tray 602. Since tray 602 is on the outside of the pouch, tray 602 is sometimes called an external tray or exo tray 602.

For simplicity, device 100 and profiled pouch 102 of FIG. 2 are discussed as being contained within tray 602 and generally within exo tray packing system 600. However, in light of this disclosure, those of skill in the art will understand that exo tray packing system 600 contains other devices and/or pouches in other embodiments depending upon the particular application. Generally, device 100 sealed within profiled pouch 102 is sometimes called a pouched device 100/102.

Tray 602 includes a first tray half 606 and a second tray half 608. Tray halves 606, 608 are formed of a rigid yet compliant material such as plastic or other packaging materials. In one embodiment, first tray half 606 is a mirror image of second tray half 608. However, first tray half 606 may include features different from second tray half 608.

First tray half 606 includes a rigid distal portion 610A including distal stiffeners 612A, locking snaps 614A, unloading snaps 616A, an unloading handle 618A, a flex feature 620A, and a cavity 622A. Second tray half 608 includes a rigid distal portion 610B including distal stiffeners 612B, locking snaps 614B, unloading snaps 616B, an unloading handle 618B, a flex feature 620B, and a cavity 622B complimentary to distal stiffeners 612A, locking snaps 614A, unloading snaps 616A, unloading handle 618A, flex feature 620A, and cavity 622A of first tray half 606, respectively. Collectively, rigid distal portions 610A, 610B, distal stiffeners 612A, 612B, locking snaps 614A, 614B, unloading snaps 616A, 616B, unloading handles 618A, 618B, flex features 620A, 620B, and cavities 622A, 622B are referred to as rigid distal portion 610, distal stiffeners 612, locking snaps 614, unloading snaps 616, opposed unloading handles 618, a flex feature 620, and a cavity 622, respectively.

Figure 9:
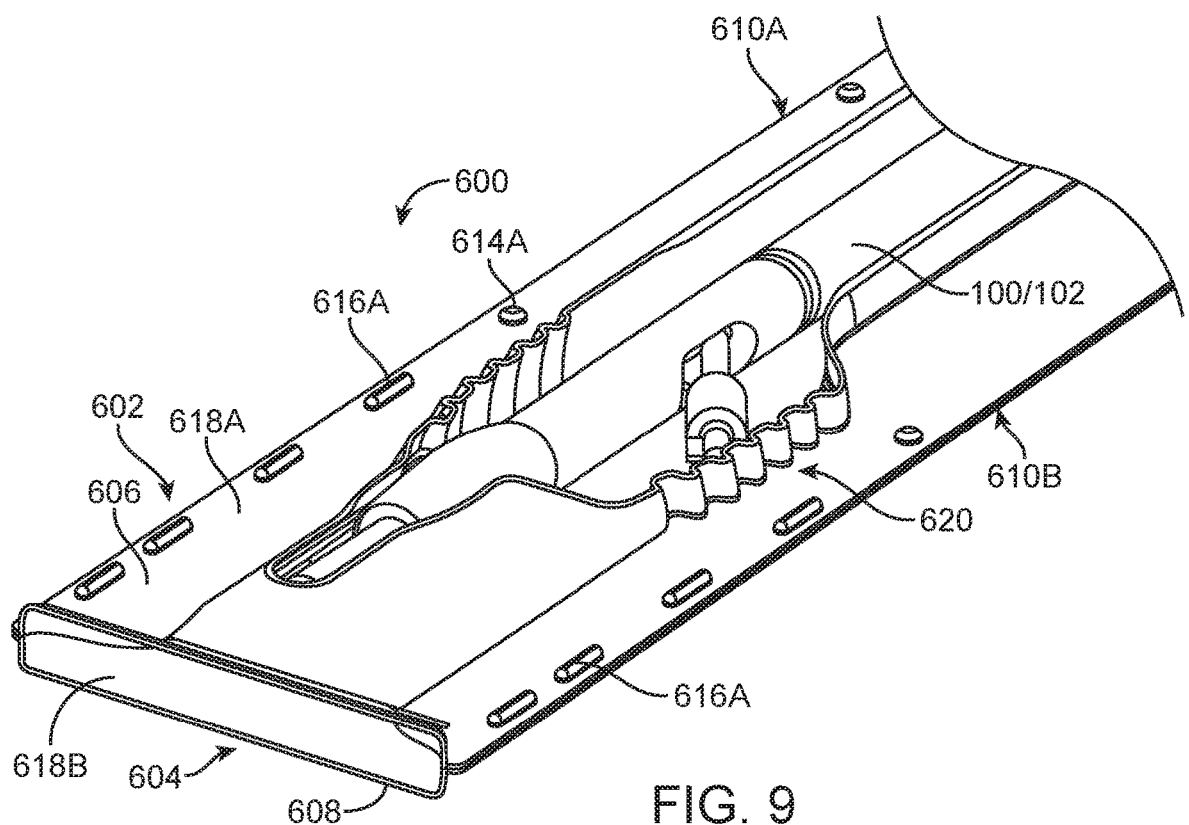
FIG. 9 is a partially cutaway perspective end view of the system of FIGS. 6-8 in accordance with an embodiment.
Figure 10:
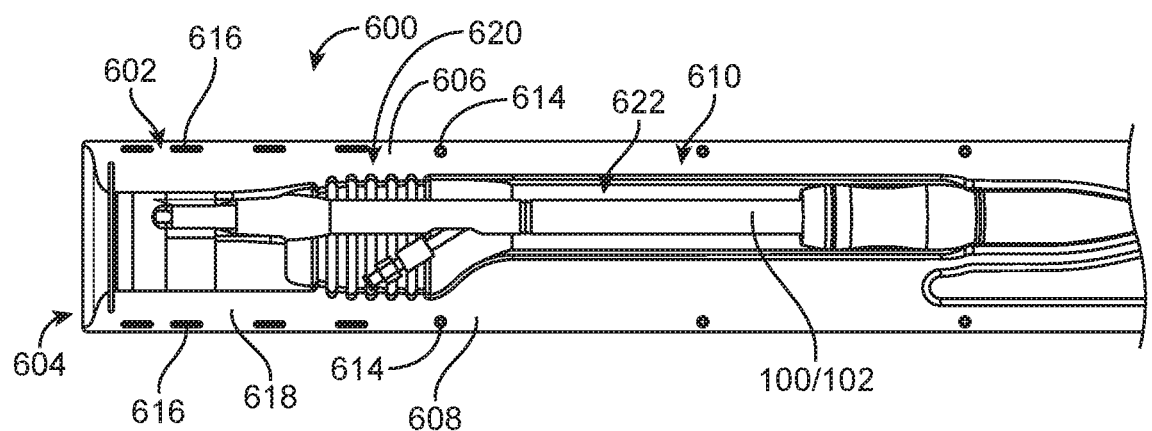
FIG. 10 is a partially cutaway top plan end view of the system of FIGS. 6-8 in accordance with an embodiment.

FIG. 9 is a partially cutaway perspective end view of system 600 of FIGS. 6-8 in accordance with an embodiment. FIG. 10 is a partially cutaway top plan end view of system 600 of FIGS. 6-8 in accordance with an embodiment. In FIGS. 9 and 10, first tray half 606 is cutaway and profiled pouch 102 is not illustrated for clarity of view of device 100 but it is to be understood that device 100 is within profiled pouch 102 (see FIG. 2) and pouched device 100/102 (device 100 sealed within profiled pouch 102) are contained within cavity 622 of tray 602.

More particularly, after pouched device 100/102 is placed within either of cavities 622A, 622B of first or second halves 604, 606, first tray half 606 is permanently coupled to second tray half 608 by locking snaps 614. Locking snaps 614 are complimentary features of first tray half 606 and second tray half 608 that when snapped together remain permanently bound. However, in other embodiments, first tray half 606 is permanently coupled to second tray half 608 using mechanical fasteners, e.g. staples, adhesive, tape, heat welded, etc.

Cavity 622 of tray 602 follows the profile of pouched device 100/102. More particularly, once profiled pouch 102 is sealed, pouched device 100/102 is placed in tray 602 which mirrors the profile of pouched device 100/102. Tray halves 604, 606 lock together by locking snaps 614 to create a fitted rigid case completely encasing the pouched device 100/102. Although cavity of tray 602 follows the profile of pouched device 100/102, in other embodiments, other pouched device are placed within tray 602, e.g., cavity 622 accommodates but does not necessarily follow the profile of the pouched device, e.g., cavity 622 is larger than the pouched device.

Tray 602 shields the sterile barrier of profiled pouch 102 from impacts and abrasion. Energy is transferred into system 600 during shipping. High energy components transfer energy to lower energy components, which absorb and/or transfer the energy until equilibrium is achieved. Relative movement between components, the area over which the energy is transferred, material, and the physical properties of the device and packaging, amongst other physical characteristics, may define the energy transfer path and conversions mechanisms.

By designing tray 602 to work with an Exo Tray-optimized carton, the system 600 may be more effective in dissipating energy than traditional free-floating packaging before the energy reaches the sterile barrier of profiled pouch 102. By mating tray 602 snuggly around pouched device 100/102, the energy differential between the components lessens significantly. Pouch abrasion, which results from energy dissipation through sliding frictional forces as the components move relative to each other, drops. Punctures, which result from forces transferred across a small cross-sectional area, become less severe when the components are coupled. Also, custom fitting tray 602 to mirror the profile of pouched device 100/102 may increase the number of touch points and the area engaged in transferring energy. Since energy must equalize (conservation of energy), increasing the number and/or the total area of the touch point may reduce the harmful effects of the transfer.

Figure 11:
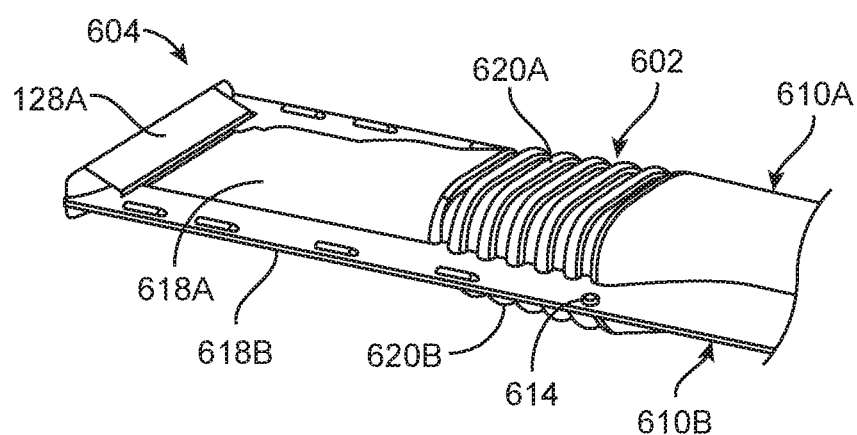
FIG. 11 is an enlarged perspective view of the proximal end of the tray including peeling panels of the profiled pouch according to an embodiment.

FIG. 11 is an enlarged perspective view of proximal end 604 of tray 602 including peeling panels 128 of profiled pouch 102 according to an embodiment. Referring now to FIG. 11, peeling panels 128 extend between and outside of opposed unloading handles 618 and are fixed to unloading handles 618. More particularly, there are two peeling panels 128, a first (upper) peeling panel 128A and a second (lower) peeling panel 128B. First peeling panel 128A is attached to unloading handle 618A and second peeling panel 128B is attached to unloading handle 618B.

Figure 12:
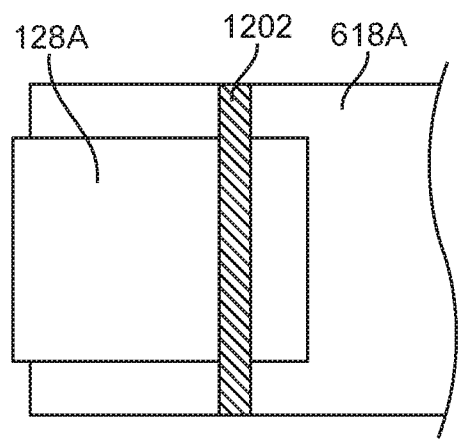
FIG. 12 is a top plan view of a peeling panel attached to an unloading handle according to an embodiment.

FIG. 12 is a top plan view of peeling panel 128A attached to unloading handle 618A according to an embodiment. As illustrated in FIG. 12, peeling panel 128A extends proximally past unloading handle 618A and is attached to the outside thereof. In one embodiment, peeling panel 128A is mechanically attached to unloading handle 618A. For example, an elastic band 1202 wraps around peeling panel 128A and unloading handle 618A thus attaching peeling panel 128A to unloading handle 618A. Although an elastic band 1202 is illustrated, in other embodiments, adhesive, staples, or other mechanical fasteners are used to attached peeling panel 128A to unloading handle 618A.

Figure 13:
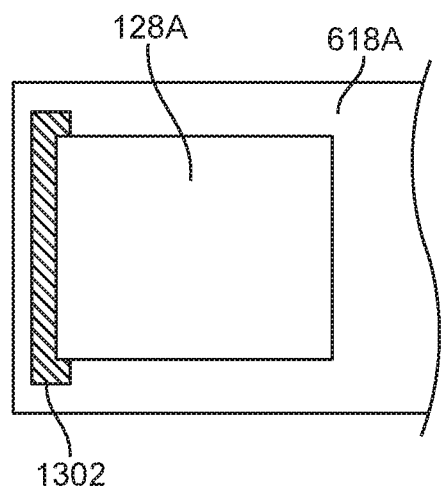
FIG. 13 is a top plan view of the peeling panel attached to the unloading handle according to another embodiment.

FIG. 13 is a top plan view of peeling panel 128A attached to unloading handle 618A according to another embodiment. As illustrated in FIG. 13, peeling panel 128A extends through a slot 1302 in unloading handle 618A and is attached to the outside thereof. Although a single linear slot 1302 is illustrated, in other embodiments, a plurality of slots, a shaped slot with complimentary shaped peeling panel 128A, or other designs to attach peeling panel 128A to unloading handle 618A are used.

Although attachment of peeling panel 128A to unloading handle 618A is discussed above and illustrated in FIGS. 12 and 13 in accordance with various embodiments, the discussion and illustrations are equally applicable to attachment of peeling panel 128B to unloading handle 618B.

Referring to FIG. 11 again, once peeling panels 128 are attached to unloading handles 618, unloading handles 618 are pressed and snapped together by unloading snaps 616. Unloading snaps 616 hold unloading handles 618 together with peeling panels 128 in between.

Unloading snaps 616 are designed so that when the user pulls unloading handles 618 with peeling panels 128 attached thereto apart, unloading snaps 616 release allowing unloading handles 618 and peeling panels 128 to be separated. More particularly, unloading snaps 616 are releasable. Flex feature 620 is flexible allowing unloading handles 618 to move relative to rigid distal portion 610. Generally, flex feature 620 is more flexible than unloading handles 618 and rigid distal portion 610 allowing flex feature 620 to flex relative to unloading handles 618 and rigid distal portion 610. In the illustrated embodiment, flex feature 620 has an accordion shape having an alternating repeating series of ridges and furrows. Flex feature 620 is sometime said to be corrugated. In another embodiment, flex feature 620 is thinner and more flexible than unloading handles 618 and rigid distal portion 610 and/or formed of a more flexible material.

Unloading handles 618 extend proximally from flex feature 620 and rigid distal portion 610 extends distally from flex feature 620. Rigid distal portion 610 includes one or more distal stiffeners 612 to enhance rigidity of rigid distal portion 610.

Figure 15:
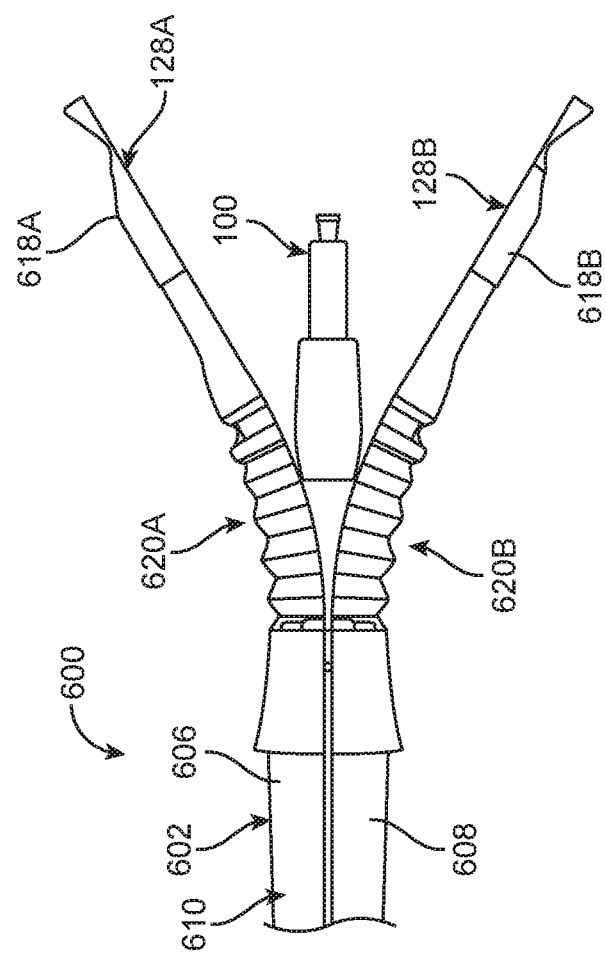
FIG. 15 is a side view of the system during exposure and removal of the device from the profiled pouch and the tray of FIG. 14 in accordance with one embodiment.
Figure 14:
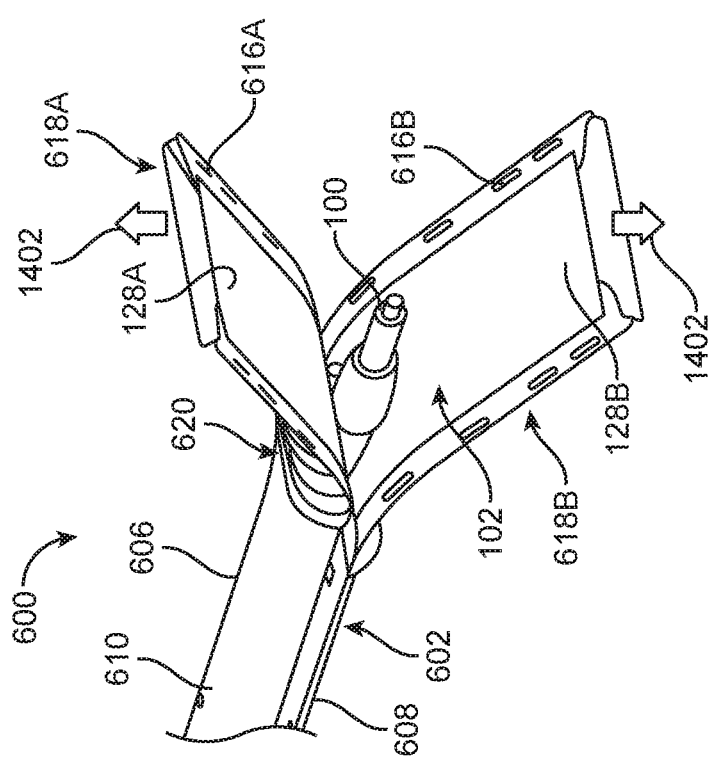
FIG. 14 is a perspective view of the system during exposure and removal of the device from the profiled pouch and the tray in accordance with one embodiment.
Figure 17:
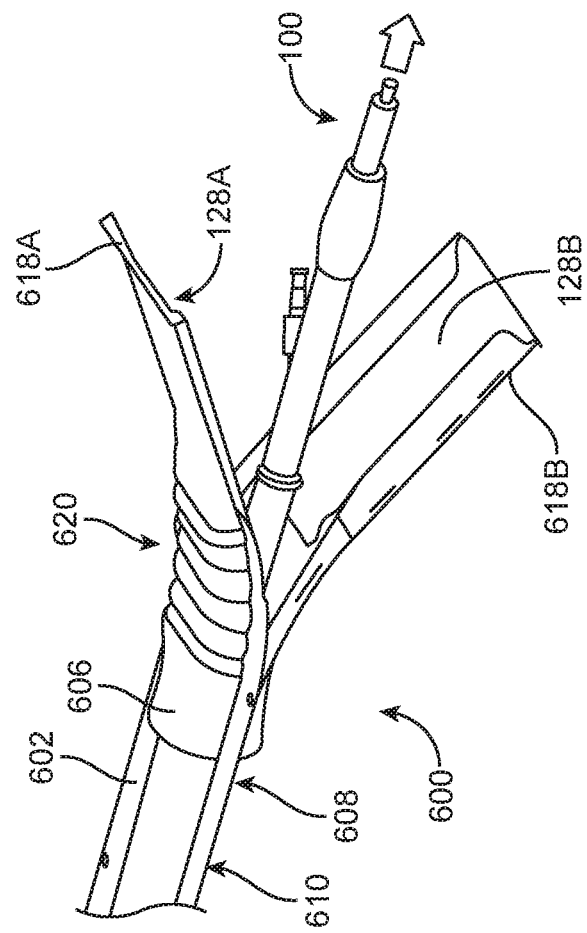
FIG. 17 is a perspective view of the system at a later stage during removal of the device from the profiled pouch and the tray in accordance with one embodiment.
Figure 16:
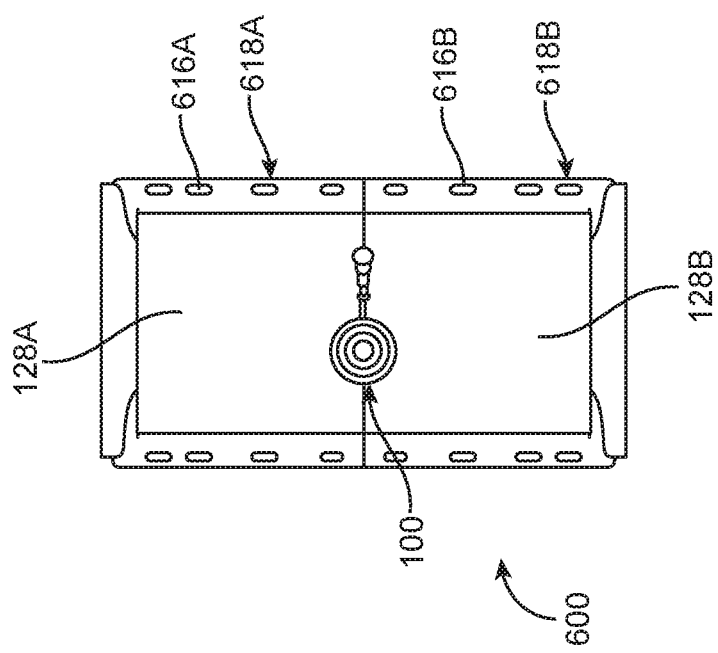
FIG. 16 is an end view of the system during exposure and removal of the device from the profiled pouch and the tray of FIG. 14 in accordance with one embodiment.
Figure 18:
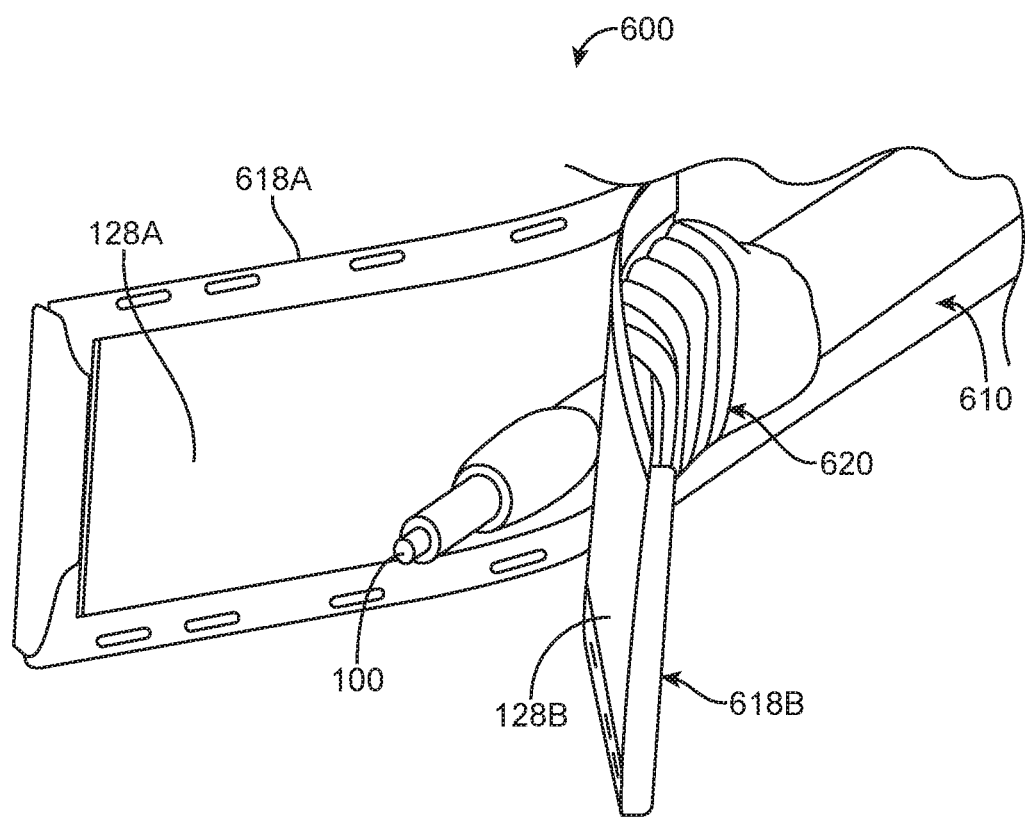
FIG. 18 is a perspective view of the system at a later stage during removal of the device from the profiled pouch and the tray in accordance with another embodiment.

FIG. 14 is a perspective view of system 600 during exposure and removal of device 100 from profiled pouch 102 and tray 602 in accordance with one embodiment. FIG. 15 is a side view of system 600 during exposure and removal of device 100 from profiled pouch 102 and tray 602 of FIG. 14 in accordance with one embodiment. FIG. 16 is an end view of system 600 during exposure and removal of device 100 from profiled pouch 102 and tray 602 of FIG. 14 in accordance with one embodiment. FIG. 17 is a perspective view of system 600 at a later stage during removal of device 100 from profiled pouch 102 and tray 602 in accordance with one embodiment. FIG. 18 is a perspective view of system 600 at a later stage during removal of device 100 from profiled pouch 102 and tray 602 in accordance with another embodiment.

Referring now to FIGS. 14-16 together, the user, e.g., circulating nurse, separates unloading handles 618 including peeling panels 128 attached thereto, see the arrows 1402 in FIG. 14 for example. Unloading snaps 616 release and flex feature 620 flexes and bends thus allowing unloading handles 618 to be separated while rigid distal portions 610A, 610B are held together by locking snaps 614.

This simultaneously opens profiled pouch 102 and exposes device 100. More particularly, peeling panels 128 are separated and open opening seal 134 (see FIG. 2). Accordingly, separating unloading handles 618 simultaneously opens profiled pouch 102, enabling aseptic transfer and removal of device 100 as illustrated in FIG. 17. FIG. 18 is a view similar to the view of FIG. 14 with tray 602 rotated ninety degrees to minimize potential contamination during aseptic transfer and removal of device 100.

Consider the traditional Carton-Pouch-Tray device configuration. From a quality perspective, device contamination can occur when during aseptic presentation, the tray holding the device, touches the nonsterile pouch exterior.

In the Exo-Tray packaging system 600, the peeling panels 128, sometimes called the peel end, of profiled pouch 102 join to tray 602. By separating unloading handles 618, sometimes called the two faces, of tray 602, the circulating nurse simultaneously opens profiled pouch 102 and exposes device 100. The scrub nurse then pulls device 100 into the sterile field as the circulating nurse maintains control of the rigid, non-sterile, non-biowaste packaging or tray 602 and profiled pouch 102. Postoperative, the spent device 100 can be inserted back into tray 602 and profiled pouch 102 trapping the biowaste prior to removal from the operating room. Tray 602 improves the ease and speed of the process while enhancing safety for both the patient and medical staff.

As set forth above, there are several clear differences between the traditional carton-pouch-tray-device system and the Exo Tray packaging system 600: the relative placement of tray and profiled pouch, the tray design, and the aseptic transfer method. In the Exo Tray packaging system 600, the device is first placed in a pouch, such as the Profiled Sterile Barrier Pouch, above.

The Exo tray concept is a complete reversal from traditional terminally sterilized medical device packaging, where the most critical safety component, the sterile barrier pouch, is also the component subjected to the most destructive energy. By placing the pouch inside a rigid, energy deflecting and absorbing shell, the likelihood of a sterile barrier breach may be reduced.

Current inside-the-pouch medical device tray designs prioritize protecting the device from shipping damage. Limited emphasis is given to tray interaction with the pouch other than minimizing sharp edges and corners. Except for the Profiled Sterile Barrier Pouch (described above), the pouch is rectangular and flat, the pouch must be sized much larger than the 3-dimensional tray/device. The Exo tray features may allow package designers to redirect and neutralize much of the damaging energy transfer and absorption that occurs across the sterile barrier in previous designs.

The Exo Tray may include snaps used to create a 3-dimensional articulating enclosure. The Exo Tray may also include an accordion flex feature, such as flex feature 620 described above, that allows the two halves of the tray to flex during opening. The accordion flex feature, snaps, unloading handles, and fixing the opening end flaps of the pouch to the tray may work in concert to eliminate the most common source of device contamination—contact with nonsterile packaging material. This design also improves the speed of aseptic transfer, a critical customer objective.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A packaging system comprising:
   a tray comprising:
   a rigid portion;
   opposed unloading handles;
   a flex feature allowing the unloading handles to move relative to the rigid portion, the flex feature being more flexible than the rigid portion;
   a first tray half;
   a second tray half, wherein the rigid portion comprises a rigid portion of the first tray half coupled to a rigid portion of the second tray half; and
   locking snaps permanently coupling the rigid portion of the first tray half to the rigid portion of the second tray half.

2. The packaging system of claim 1 wherein the flex feature is flexible.

3. The packaging system of claim 1 wherein the first tray half comprises a first unloading handle of the unloading handles and the second tray half comprises a second unloading handle of the unloading handles.

4. A packaging system comprising:
   a tray comprising:
   a rigid portion;
   opposed unloading handles;
   a flex feature allowing the unloading handles to move relative to the rigid portion, the flex feature being more flexible than the rigid portion;
   a first tray half;
   a second tray half, wherein the first tray half comprises a first unloading handle of the unloading handles and the second tray half comprises a second unloading handle of the unloading handles; and
   unloading snaps releasably coupling the first unloading handle to the second unloading handle.

5. The packaging system of claim 1 further comprising a medical device within a cavity of the tray.

6. The packaging system of claim 5 further comprising a pouch within the cavity, the medical device being within the pouch.

7. The packaging system of claim 6 wherein the cavity has a profile that matches a profile of the pouch and the profile of the pouch matches a profile of the medical device.

8. A packaging system comprising:
   a tray comprising:
   a rigid portion;
   opposed unloading handles; and
   a flex feature allowing the unloading handles to move relative to the rigid portion, the flex feature being more flexible than the rigid portion;
   a medical device within a cavity of the tray;
   a pouch within the cavity, the medical device being within the pouch, wherein the pouch comprises a linear seal and an opening seal hermetically sealing the medical device within the pouch, the pouch further comprising peeling panels extending proximally from the opening seal, the peeling panels being free from one another.

9. The packaging system of claim 8 wherein the peeling panels are coupled to the unloading handles.

10. The packaging system of claim 9 further comprising elastic bands coupling the peeling panels to the unloading handles.

11. The packaging system of claim 9 wherein the peeling panels pass through slots in the unloading handles.

12. The packaging system of claim 6 wherein the pouch comprises:
    two shaped sheets sealed on three sides by a linear seal, the linear seal leaving a pouch opening open for insertion of the medical device, a profile of the pouch matching a profile of the medical device.

13. The packaging system of claim 12 where the pouch further comprises:
    an opening seal, the medical device being hermetically sealed with the pouch by the linear seal and the opening seal; and
    peeling panels extending proximally from the opening seal, the peeling panels being free from one another.

14. The packaging system of claim 13 wherein the pouch further comprises a flared peeling portion, the flared peeling portion comprising wide mouth portions and the peeling panels.

15. The packaging system of claim 1 where the rigid portion extends distally from the flex feature and the unloading handles extend proximally from the flex feature.

\* \* \* \* \*